United States Patent
Oleson et al.

(10) Patent No.: US 10,327,499 B1
(45) Date of Patent: Jun. 25, 2019

(54) SYSTEM AND METHOD FOR CONTROLLING ACTIVE RECOVERY BASED ON DETECTED PARAMETER

(71) Applicant: Under Armour, Inc., Baltimore, MD (US)

(72) Inventors: Mark A. Oleson, Baltimore, MD (US);
F. Grant Kovach, Baltimore, MD (US);
Nathan Dau, Baltimore, MD (US);
Jeffrey Allen, Baltimore, MD (US)

(73) Assignee: Under Armour, Inc., Baltimore, MD (US)

( * ) Notice: Subject to any disclaimer, the term of this patent is extended or adjusted under 35 U.S.C. 154(b) by 360 days.

(21) Appl. No.: 15/213,749

(22) Filed: Jul. 19, 2016

(51) Int. Cl.
| | |
|---|---|
| *G06F 17/00* | (2019.01) |
| *A43B 3/00* | (2006.01) |
| *A61B 5/021* | (2006.01) |
| *A61B 5/0205* | (2006.01) |
| *A61B 5/00* | (2006.01) |
| *A43B 13/20* | (2006.01) |
| *G05B 15/02* | (2006.01) |

(52) U.S. Cl.
CPC ............ *A43B 3/0005* (2013.01); *A43B 13/20* (2013.01); *A61B 5/0024* (2013.01); *A61B 5/021* (2013.01); *A61B 5/02055* (2013.01); *G05B 15/02* (2013.01)

(58) Field of Classification Search
CPC ....... G01L 1/205; A43B 3/0005; A43B 13/20; A43B 7/1455; A43B 7/1475; A61B 5/02055; A61B 5/021; A61B 5/0024; A61B 2562/166; A61B 2562/164; A61B 2562/0247; A61B 2503/10; A61B 5/6807
See application file for complete search history.

(56) References Cited

U.S. PATENT DOCUMENTS

| | | | | |
|---|---|---|---|---|
| 2017/0273615 A1* | 9/2017 | Oleson | ................... | A61B 5/486 |
| 2017/0273849 A1* | 9/2017 | Oleson | ................... | A61H 1/008 |

* cited by examiner

*Primary Examiner* — Hsien Ming Lee
(74) *Attorney, Agent, or Firm* — Maginot, Moore & Beck LLP

(57) ABSTRACT

A shoe is provided for use by a user and for use with a communication device that transmits a blood pressure signal based on a detected blood pressure of the user. The shoe includes a sole, a force actuating mechanism, a receiver and a controller. The sole has a top surface for supporting the foot of the user when being worn by the user. The force actuating mechanism provides a force normal to the top surface of the sole and is disposed at the sole so as to provide the force to a plantar venous plexus of the foot. The receiver receives the blood pressure signal. The controller generates a control signal to control the force actuating mechanism. The controller further modifies the control signal based on the received blood pressure signal.

20 Claims, 6 Drawing Sheets

SYSTEM AND METHOD FOR CONTROLLING ACTIVE RECOVERY BASED ON DETECTED PARAMETER

BACKGROUND

The present invention generally relates to devices and methods to improve blood flow and recovery.

There exists a need for a device and method to improve blood flow and speed recovery based on detected parameters.

BRIEF SUMMARY OF THE DRAWINGS

The accompanying drawings, which are incorporated in and form a part of the specification, illustrate example embodiments and, together with the description, serve to explain the principles of the invention. In the drawings:

FIGS. 1A-B illustrate the plantar venous plexus, wherein FIG. 1A illustrates a bottom view of a foot and FIG. 1B illustrates a side view of the foot;

DETAILED DESCRIPTION

Overview

A shoe is provided for use by a user and for use with a communication device that is operable to transmit a blood pressure signal based on a detected blood pressure of the user. The shoe includes a sole, a force actuating mechanism, a receiver and a controller. The sole has a top surface for supporting the foot of the user when being worn by the user. The force actuating mechanism provides a force normal to the top surface of the sole. The force actuating mechanism is disposed at the sole so as to provide the force to a plantar venous plexus of the foot. The receiver receives the blood pressure signal. The controller generates a control signal to control the force actuating mechanism. The controller is further operable to modify the control signal based on the received blood pressure signal.

Example Embodiments

Figure 1A:
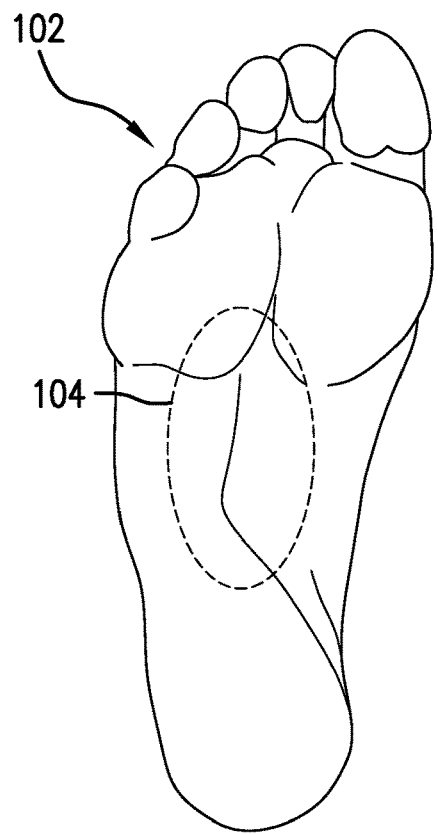
Figure 1B:
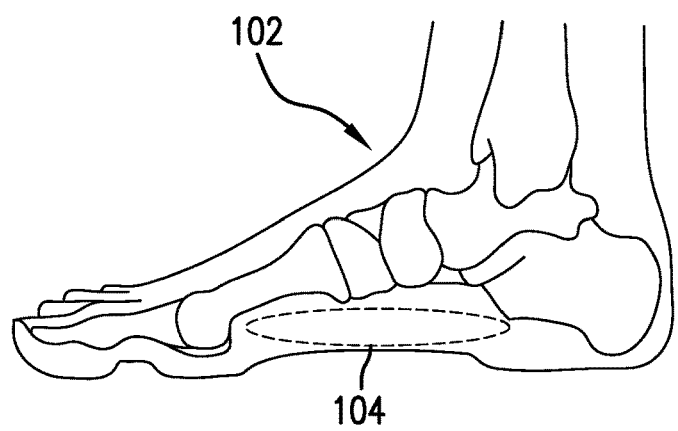

FIGS. 1A-B illustrate the plantar venous plexus, wherein FIG. 1A illustrates a bottom view of a foot and FIG. 1B illustrates a side view of the foot.

As shown in the figures, a plantar venous plexus 104 is generally located in the central portion of the plantar side of a foot 102.

Plantar venous plexus 104 is an area of foot 102 that functions to pump blood back up the leg from the foot and is also known as the venous foot pump. Typically, plantar venous plexus 104 is directly involved with the action of walking, with the pressures exerted on the foot during the walking cycle serving to effectively pump the blood. The purpose is to pump deoxygenated blood up the leg to the next stage pump, called the calf pump. The pumping action serves to take blood that has delivered nutrients to the foot and move the blood back toward the heart and lungs, taking all the waste products with it.

Problems may arise, though, after a person has a strenuous workout and desires to rest and recover. While the person is resting, plantar venous plexus 104 is not effectively pumping blood and is therefore ineffectively disposing of waste products. As such, the waste products pool in the foot and lower leg. There exists a need for a device and method to effectively pump blood through the plantar venous plexus and support recovery after engaging in athletic activity.

Figure 2:
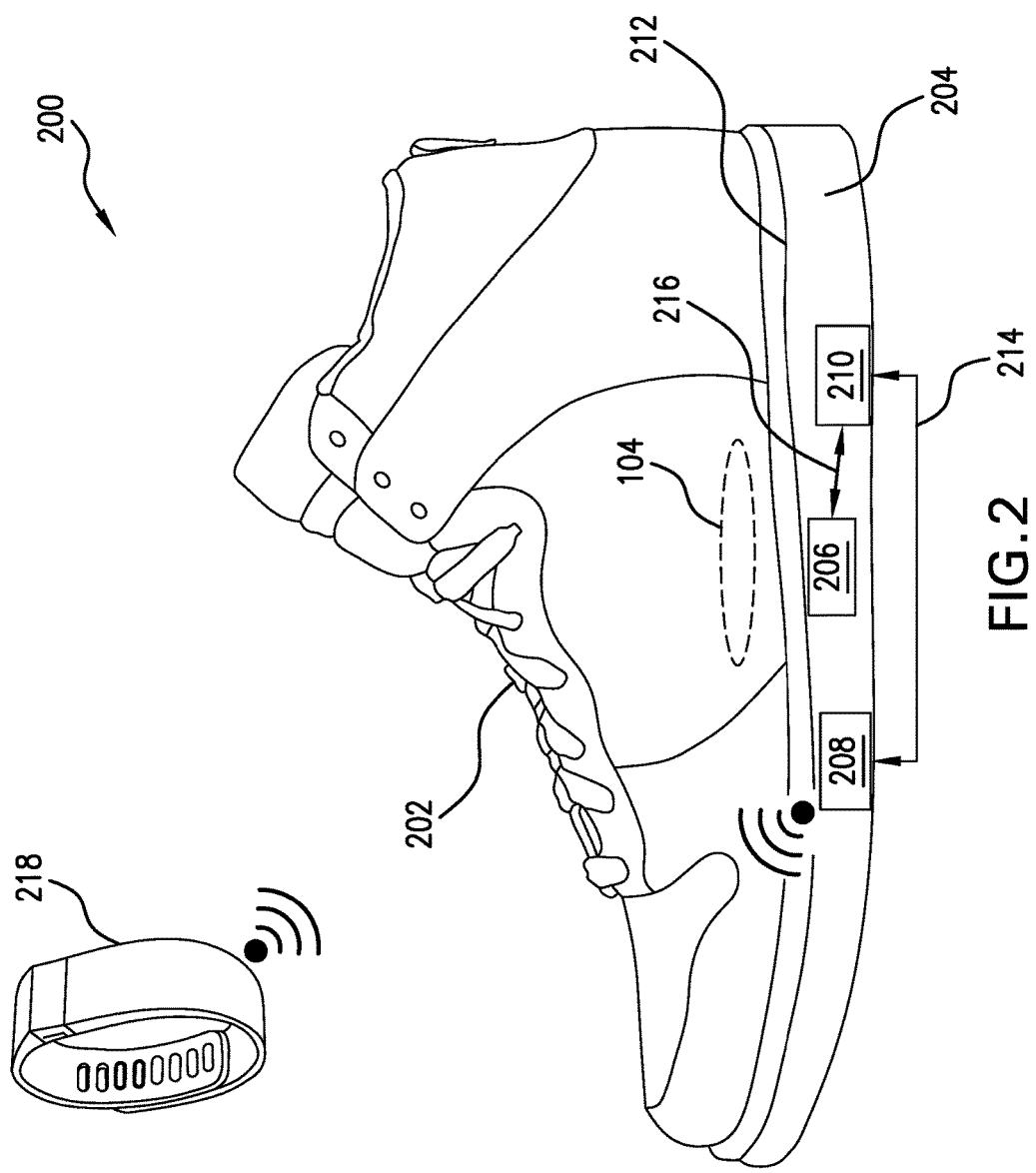
FIG. 2 illustrates a shoe in accordance with aspects of the present invention.

FIG. 2 illustrates a shoe in accordance with aspects of the present invention.

As shown in the figure, a system 200 includes a shoe 202 and a communication device 218. Shoe 202 further includes a force actuating mechanism 206, a receiver 208, a controller 210 and a sole 204. Sole 204 further includes a top surface 212. Communication device 218 can be any device that can detect a parameter and transmit signals based on the detected parameter including, but not limited to, an activity monitoring device, a smartwatch, a cellular telephone and a tablet computer. Transmitting data may be accomplished via wireless means including, but not limited to, Bluetooth and WiFi.

Communication device 218 detects a parameter and wirelessly transmits signals based on the parameter to receiver 208. The detected parameter can be any number of parameters including, but not limited to, blood pressure, heart rate, temperature, moisture, salinity and breathing rate.

Receiver 208 receives signals from communication device 218 and sends those signals to controller 210 via line 214.

Controller 210 receives communications from receiver 208 via line 214, and provides instructions to force actuating mechanism 206 via line 216. The instructions provided to force actuating mechanism 206 are based on the communications from receiver 208.

Force actuating mechanism 206 receives instructions from controller 210 via line 216 and executes those instructions received from controller 210, resulting in force actuating mechanism 206 extending or retracting. Force actuating mechanism 206 is in contact with top surface 212. As force actuating mechanism 206 extends, it exerts a force on plantar venous plexus 104 and as it retracts, it releases the force exerted on plantar venous plexus 104. Force actuating mechanism 206 can be any type of known actuator that can extend or retract, including, but not limited to, hydraulic, pneumatic, electric, thermal, magnetic or mechanical.

As shown in the figure, force actuating mechanism 206, receiver 208 and controller 210 are shown as separate elements. However, in some embodiments, at least two of force actuating mechanism 206, receiver 208 and controller 210 may be combined as a unitary device.

In some embodiments, at least one of force actuating mechanism 206, receiver 208 and controller 210 may be implemented as a computer having tangible computer-readable media for carrying or having computer-executable instructions or data structures stored thereon. Such tangible computer-readable media can be any available media that can be accessed by a general purpose or special purpose computer. Non-limiting examples of tangible computer-readable media include physical storage and/or memory media such as RAM, ROM, EEPROM, CD-ROM or other optical disk storage, magnetic disk storage or other magnetic storage devices, or any other medium which can be used to carry or store desired program code means in the form of computer-executable instructions or data structures and which can be accessed by a general purpose or special purpose computer. For information transferred or provided over a network or another communications connection (either hardwired, wireless, or a combination of hardwired or wireless) to a computer, the computer may properly view the connection as a computer-readable medium. Thus, any such connection may be properly termed a computer-readable medium. Combinations of the above should also be included within the scope of computer-readable media.

The operation of system 200 will be further described with reference to FIG. 6.

Figure 3:
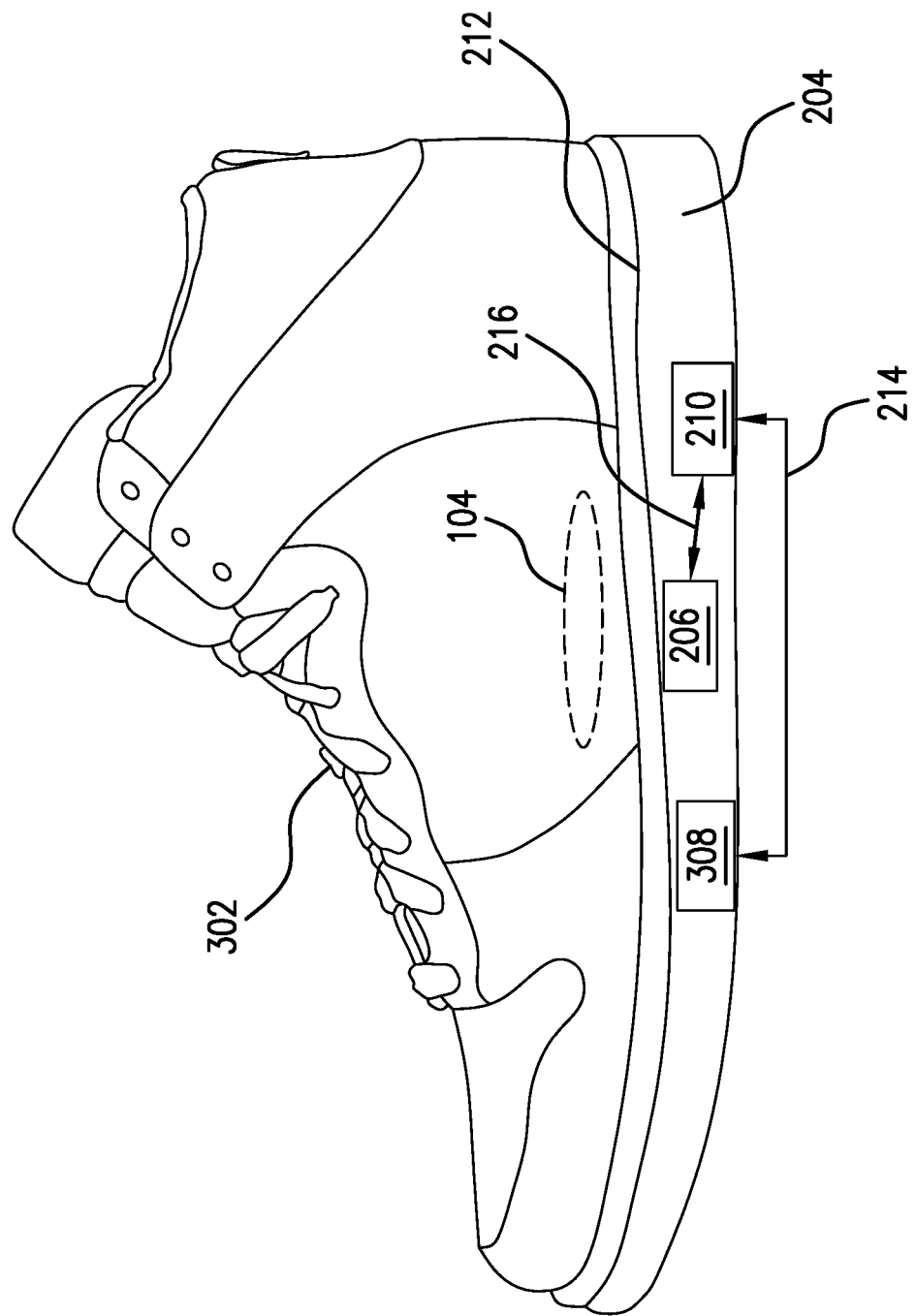
FIG. 3 illustrates another shoe in accordance with other aspects of the present invention.

FIG. 3 illustrates another shoe in accordance with other aspects of the present invention;

As shown in the figure, a shoe 302 includes a detector 308.

Detector 308 detects a parameter, generates a signal based on the parameter and provides the signal to controller 210 via line 214.

In some embodiments, at least one of force actuating mechanism 206, detector 308 and controller 210 may be implemented as a computer having tangible computer-readable media for carrying or having computer-executable instructions or data structures stored thereon. Such tangible computer-readable media can be any available media that can be accessed by a general purpose or special purpose computer.

The operation of shoe 302 will be further described with reference to FIG. 6.

Figure 4A:
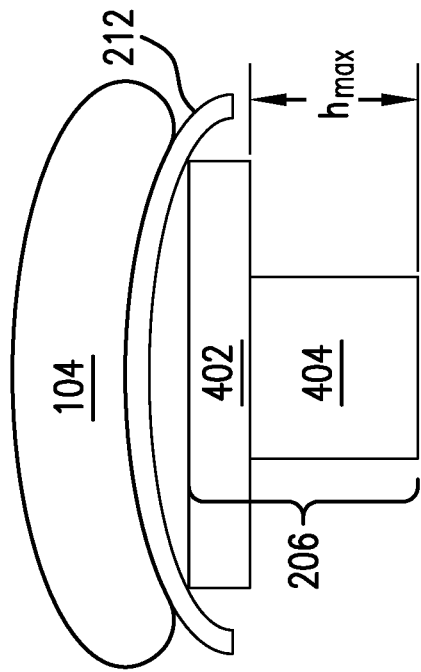
FIGS. 4A-B illustrate a force actuating mechanism in retracted and extended states in accordance with aspects of the present invention.
Figure 4B:
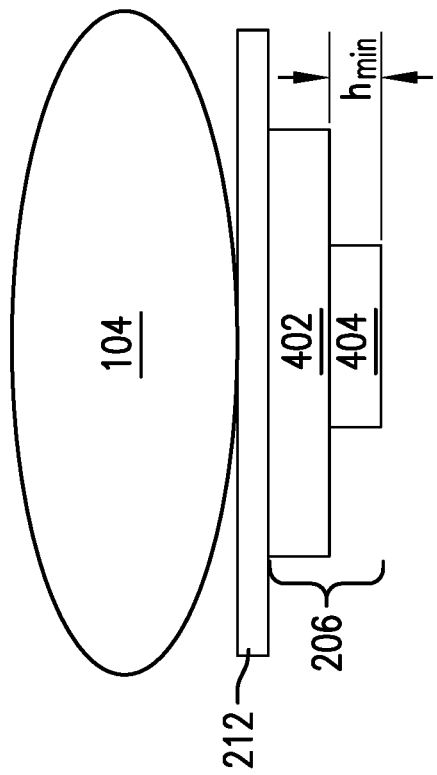

FIGS. 4A-B illustrate a force actuating mechanism in retracted and extended states in accordance with aspects of the present invention.

As shown in the figures, force actuating mechanism 206 includes a surface 402 and an extending mechanism 404. Surface 402 is in contact with both extending mechanism 404 and top surface 212.

As shown in FIG. 4A, force actuating mechanism 206 is in a retracted state with the height of extending mechanism 404 denoted by height $h_{min}$. In this configuration, surface 402 is not pushing against sole 212 and sole 212 is not pushing against the foot of the wearer.

With extending mechanism 404 not pushing against the foot of the wearer, plantar venous plexus 104 is not compressed, meaning that force actuating mechanism 206 is not acting to pump blood through plantar venous plexus 104.

As shown in FIG. 4B, force actuating mechanism 206 is in an extended state with the height of extending mechanism 404 denoted by height $h_{max}$. In this configuration, surface 402 is pushing against sole 212 and sole 212 is pushing against the bottom of the foot of the wearer. With extending mechanism 404 pushing against the foot of the wearer, plantar venous plexus 104 is compressed, meaning that force actuating mechanism 206 is acting to pump blood through plantar venous plexus 104.

The operation of force actuating mechanism 206 moving from a retracted to an extended state will be further described with reference to FIGS. 5-6.

Figure 5:
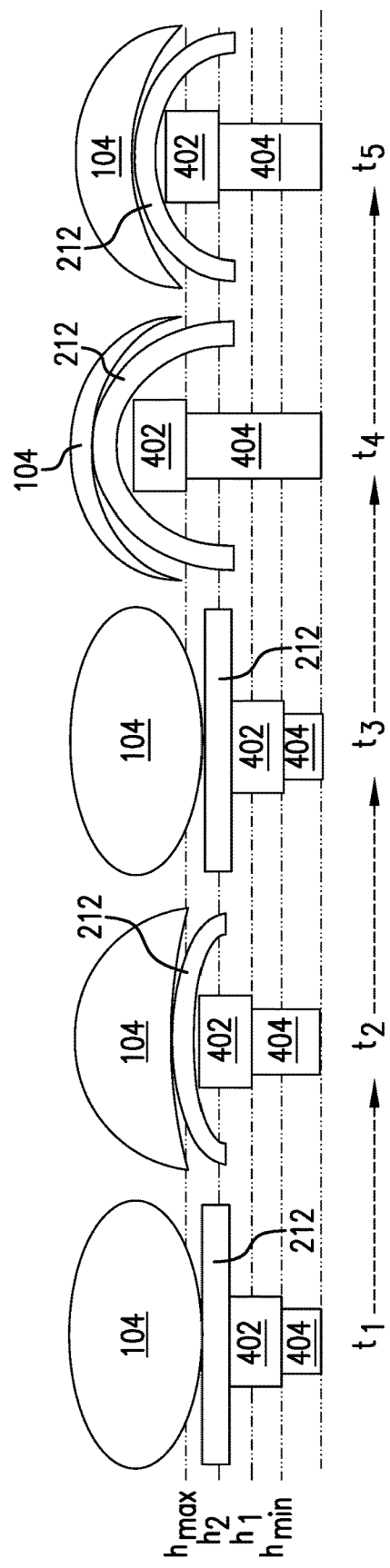
FIG. 5 illustrates a force actuating mechanism in retracted and extended states over time in accordance with aspects of the present invention.

FIG. 5 illustrates a force actuating mechanism in retracted and extended states over time in accordance with aspects of the present invention.

As shown in the figure, at time $t_1$ extending mechanism 404 is at height $h_{min}$, indicating that extending mechanism 404 is in the fully retracted state. At some time later, $t_2$, extending mechanism 404 has moved to height $h_1$, pushing surface 402 into sole 212 and as sole 212 is forced upwards, it pushes against plantar venous plexus 104, aiding blood flow. At a later time, $t_3$, extending mechanism 404 is once again at height $h_{min}$, the fully retracted state, wherein plantar venous plexus 104 is not acting to aid blood flow. At a further later time, $t_4$, extending mechanism 404 is at height $h_{max}$, indicating that extending mechanism 404 is in the fully extended state. In the fully extended state, sole 212 is forced against plantar venous plexus 104 to the maximum allowable amount, aiding blood flow during active recovery. At a later time, $t_5$, extending mechanism 404 is at height $h_2$, forcing sole 212 against plantar venous plexus 104, aiding blood flow.

The process by which extending mechanism 404 moves between $h_{min}$ and $h_{max}$ will be further described with reference to FIG. 6.

Figure 6:
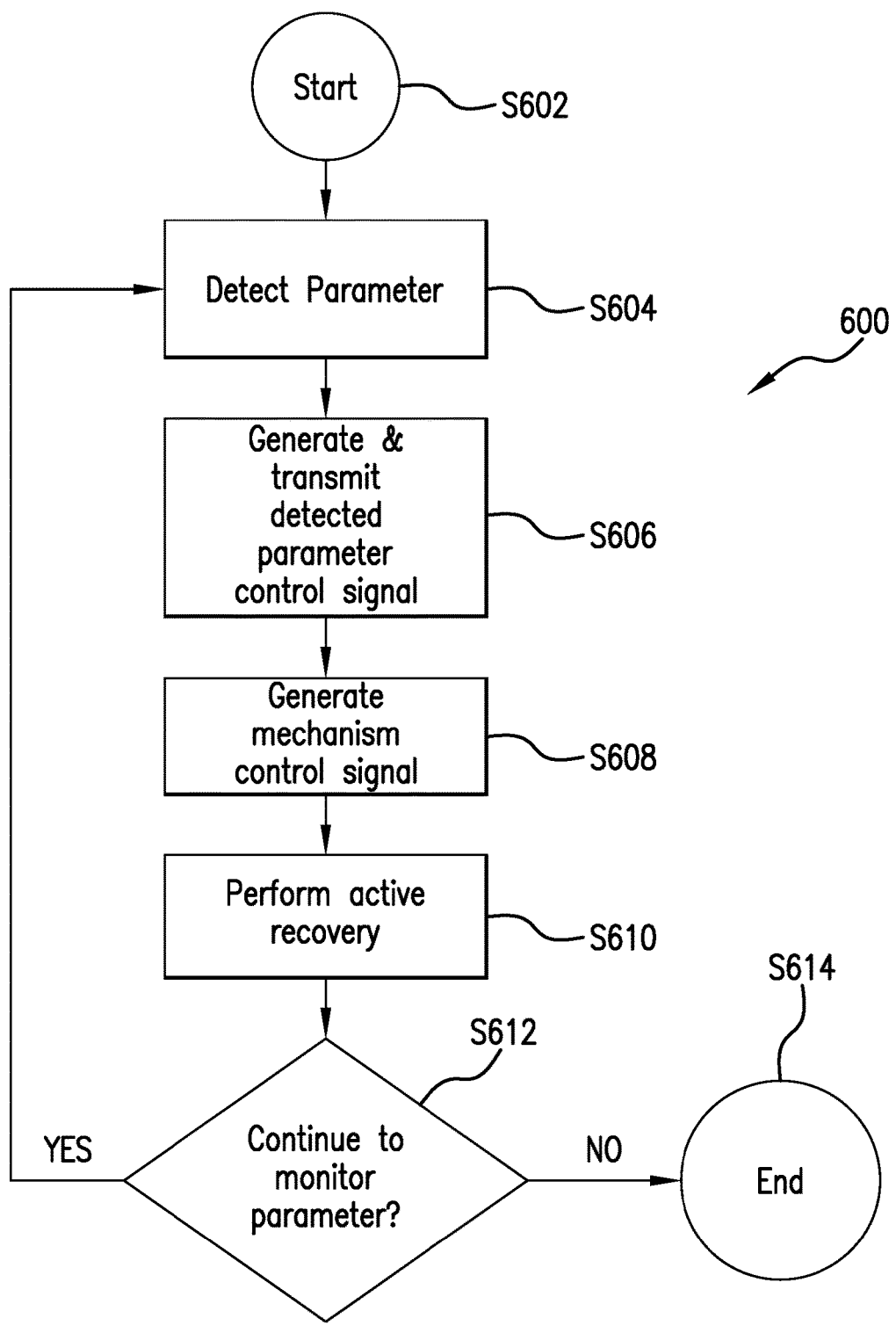
FIG. 6 illustrates a process by which active recovery is achieved in response to a detected parameter in accordance with aspects of the present invention.

FIG. 6 illustrates a process by which active recovery is achieved in response to a detected parameter in accordance with aspects of the present invention.

As shown in the figure, process 600 starts (S602), and a parameter is detected (S604).

For example, returning to FIG. 2, the user has finished a strenuous exercise and desires to engage in active recovery. The user puts on shoe 202 to begin active recovery. In this example, the active recovery is based on a parameter detected by communication device 218, which the user is wearing. For purposes of discussion, communication device 218 is detecting the user's blood pressure.

Referring back to FIG. 5, the time when the user puts on shoe 202 corresponds with time $t_1$ where extending mechanism 404 is fully retracted.

Returning to FIG. 2, communication device 218 detects the user's blood pressure.

In an alternate embodiment, and with reference to FIG. 3, the user may put on shoe 302 to engage in active recovery. When the user puts on shoe 302, detector 308 detects the user's blood pressure.

Referring back to FIG. 6, the parameter control signal is generated and transmitted (S606).

Returning to FIG. 2, after communication device 218 detects the user's blood pressure, communication device 218 generates a parameter control signal based on the user's blood pressure. Communication device 218 then wirelessly transmits the parameter control signal to receiver 208. Receiver 208 then transmits the parameter control signal to controller 210 via line 214.

In an alternate embodiment, and with reference to FIG. 3, after detector 308 detects user's blood pressure, detector 308 generates a parameter control signal based on the user's blood pressure. Detector 308 then transmits the parameter control signal to controller 210 via line 214.

Returning to FIG. 6, the mechanism control signal is generated (S608).

Referring back to FIGS. 2-3, controller 210 receives the parameter control signal from either receiver 208 or detector 308. Controller 210 then uses the data contained in the parameter control signal to generate a mechanism control signal that is based on the user's blood pressure.

In an example embodiment, controller 210 has a memory therein (not shown) that is operable to store blood pressure relationship data to be used for determining active foot recovery parameters. For example, controller 210 may have any known data structure, a non-limiting example of which includes a look up table, wherein a blood pressure is associated with a predetermined prescribed active foot recovery.

Non-limiting examples of predetermined prescribed active foot recovery include total time of active recovery as applied by force actuating mechanism 206, duty cycle of force actuating mechanism 206 during active foot recovery, maximum height of force actuating mechanism 206 during active foot recovery, minimum height of force actuating mechanism 206 during active foot recovery, frequency of force actuating mechanism 206 during active foot recovery and combinations thereof.

For example, and for purposes of discussion, controller 210 may include data associating a systolic blood pressure of 121 mm Hg and a diastolic blood pressure of 83 mm Hg to require active foot recovery to be performed such that force actuating mechanism 206 has a 50/50 duty cycle, with a minimum height of 0 mm, a maximum height of 15 mm and a frequency of 30 Hz for a time period of 20 minutes.

Controller 310 uses the blood pressure information within the parameter control signal and the corresponding relationship data stored therein to generate the mechanism control signal. The mechanism control signal will instruct force actuating mechanism 206 how to operate during active recovery. Controller 210 transmits the mechanism control signal to force actuating mechanism 206 via line 216.

Returning to FIG. 6, active recovery is performed (S610).

Returning to FIGS. 2-3, force actuating mechanism 206 receives the mechanism control signal from controller 210 via line 216 and begins active recovery.

Referring back to FIG. 5, at time $t_1$ let the user's blood pressure be $p_1$, and the mechanism control signal instructs force actuating mechanism 206 to raise extending mechanism 404 from height $h_{min}$ at time $t_1$ to height $h_1$ at time $t_2$. During this time, sole 212 is being forced into plantar venous plexus 104, causing blood to flow and aid in active recovery.

At time $t_2$, the mechanism control signal instructs force actuating mechanism 206 to lower extending mechanism 404 from height $h_1$ at time $t_2$ to height $h_{min}$ at time $t_3$. Force actuating mechanism 206 then cycles the states shown at times $t_1$-$t_3$, to aid in active foot recovery in response to the user's blood pressure $p_1$.

Suppose, for purposes of discussion, that after performing some active recovery by cycling through the states shown at times $t_1$-$t_3$ of FIG. 5, that a new blood pressure $p_2$ is detected.

Again, controller 310 uses the blood pressure information within the parameter control signal and the corresponding relationship data stored therein to generate the mechanism control signal. The mechanism control signal will instruct force actuating mechanism 206 how to operate during active recovery. Controller 210 transmits the mechanism control signal to force actuating mechanism 206 via line 216.

In this example, suppose that for the new blood pressure $p_2$, the prescribed active recovery requires extending mechanism 404 to extend to a greater height. In such a case, the mechanism control signal instructs force actuating mechanism 206 to raise extending mechanism 404 from height $h_{min}$ at time $t_3$ to height $h_{max}$ at time $t_4$.

Further, force actuating mechanism 206 then cycles the states shown at times $t_3$ and $t_4$, for example passing through the state shown at time $t_5$ to aid in active foot recovery in response to the user's blood pressure $p_2$.

Returning to FIG. 6, the user may choose to stop monitoring blood pressure to help perform active recovery (NO at S612). If the user does so, process 600 ends (S614).

If, however, the user chooses to continue monitoring blood pressure to help perform active recovery (YES at S612), the process of detecting the blood pressure, generating and transmitting the blood pressure signal, generating and transmitting the mechanism control signal and performing active recovery continues.

This feedback loop will continue until the user's active recovery is complete.

To change the distance by which extending mechanism 404 is extended or retracted, controller 210 may modify the pulse width, pulse number or pulse amplitude of the mechanism control signal it sends to force actuating mechanism 206.

The time intervals between $t_1$ and $t_2$, $t_2$ and $t_3$, $t_3$ and $t_4$, and $t_4$ and $t_5$ may all be equal, but they may also all be different in order to accomplish an effective active recovery session. Controller 210 may change the time intervals directly by modifying the mechanism control signal it sends to force actuating mechanism 206. Controller 210 may also change the time intervals indirectly by modifying the pulse width, pulse number or pulse amplitude of the mechanism control signal it sends to force actuating mechanism 206.

Controller 210 may also change the speed at which force actuating mechanism 206 extends or retracts, which will also alter the time intervals. Further, controller 210 may modify how long force actuating mechanism 206 remains in a given position, thus altering the overall time intervals between cycles.

The foregoing description of various preferred embodiments have been presented for purposes of illustration and description. It is not intended to be exhaustive or to limit the invention to the precise forms disclosed, and obviously many modifications and variations are possible in light of the above teaching. The example embodiments, as described above, were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed as new and desired to be protected by Letters Patent of the United States is:

1. A shoe for use by a user and for use with a communication device operable to transmit a blood pressure signal based on a detected blood pressure of the user, said shoe comprising:
    a sole having a top surface for supporting the foot of the user when being worn by the user;
    a force actuating mechanism operable to provide a force normal to said top surface of said sole, said force actuating mechanism being disposed at said sole so as to provide the force to a plantar venous plexus of the foot;
    a receiver operable to receive the blood pressure signal, and
    a controller operable to generate a control signal to control said force actuating mechanism,
    wherein said controller is further operable to modify the control signal based on the received blood pressure signal.

2. The shoe of claim 1,
    wherein said force actuating mechanism comprises a surface portion and an extending mechanism,
    wherein said extending mechanism is operable to extend said surface portion from a first position to a second position, and
    wherein the second position is separated from the first position by a distance and in a direction normal to said top surface of said sole.

3. The shoe of claim 2,
wherein said controller is operable to generate the control signal so as to set the distance between the first position and the second position,
wherein said controller is operable to modify the control signal, based on the received blood pressure signal, so as to change the distance between the first position and the second position.

4. The shoe of claim 3,
wherein said controller is operable to generate the control signal so as to be a digital signal having a pulse width,
wherein said controller is operable to modify the control signal, based on the received blood pressure signal, so as to change the pulse width to change the distance between the first position and the second position.

5. The shoe of claim 3,
wherein said controller is operable to generate the control signal so as to be a digital signal having a pulse number,
wherein said controller is operable to modify the control signal, based on the received blood pressure signal, so as to change the pulse number to change the distance between the first position and the second position.

6. The shoe of claim 3,
wherein said controller is operable to generate the control signal so as to be a digital signal having a pulse amplitude,
wherein said controller is operable to modify the control signal, based on the received blood pressure signal, so as to change the pulse amplitude to change the distance between the first position and the second position.

7. The shoe of claim 2,
wherein said controller is operable to generate the control signal so as to set a time for the extending mechanism to extend said surface portion from the first position to the second position,
wherein said controller is operable to modify the control signal, based on the received blood pressure signal, so as to change the time for the extending mechanism to extend said surface portion from the first position to the second position.

8. The shoe of claim 7,
wherein said controller is operable to generate the control signal so as to be a digital signal having a pulse width,
wherein said controller is operable to modify the control signal, based on the received blood pressure signal, so as to change the pulse width to change the time for the extending mechanism to extend said surface portion from the first position to the second position.

9. The shoe of claim 7,
wherein said controller is operable to generate the control signal so as to be a digital signal having a pulse number,
wherein said controller is operable to modify the control signal, based on the received blood pressure signal, so as to change the pulse number to change the time for the extending mechanism to extend said surface portion from the first position to the second position.

10. The shoe of claim 7,
wherein said controller is operable to generate the control signal so as to be a digital signal having a pulse amplitude,
wherein said controller is operable to modify the control signal, based on the received blood pressure signal, so as to change the pulse amplitude to change the time for the extending mechanism to extend said surface portion from the first position to the second position.

11. The shoe of claim 1, further comprising:
wherein said receiver is further operable to receive a second blood pressure signal after said controller modifies the control signal based on the received blood pressure signal, and
wherein said controller is further operable to further modify the previously modified control signal based on the received second blood pressure signal.

12. A shoe for use by a user, said shoe comprising:
a sole having a top surface for supporting the foot of the user when being worn by the user;
a force actuating mechanism operable to provide a force normal to said top surface of said sole, said force actuating mechanism being disposed at said sole so as to provide the force to a plantar venous plexus of the foot;
a blood pressure detector operable to generate a blood pressure signal, and
a controller operable to generate a control signal to control said force actuating mechanism,
wherein said controller is further operable to receive the blood pressure signal and modify the control signal based on the received blood pressure signal.

13. The shoe of claim 12,
wherein said force actuating mechanism comprises a surface portion and an extending mechanism,
wherein said extending mechanism is operable to extend said surface portion from a first position to a second position, and
wherein the second position is separated from the first position by a distance and in a direction normal to said top surface of said sole.

14. The shoe of claim 13,
wherein said controller is operable to generate the control signal so as to set the distance between the first position and the second position,
wherein said controller is operable to modify the control signal, based on the received blood pressure signal, so as to change the distance between the first position and the second position.

15. The shoe of claim 13,
wherein said controller is operable to generate the control signal so as to set a time for the extending mechanism to extend said surface portion from the first position to the second position,
wherein said controller is operable to modify the control signal, based on the received blood pressure signal, so as to change the time for the extending mechanism to extend said surface portion from the first position to the second position.

16. The shoe of claim 12, further comprising:
wherein said controller is further operable to receive a second blood pressure signal after said controller modifies the control signal based on the received blood pressure signal, and
wherein said controller is further operable to further modify the previously modified control signal based on the received second blood pressure signal.

17. A non-transitory, tangible, computer-readable media having computer-readable instructions stored thereon and for use with a wireless communication device operable to transmit an blood pressure signal based on a blood pressure of a user, the computer-readable instructions being capable of being read by a computer and being capable of instructing the computer to perform the method comprising:
receiving the blood pressure signal via a receiver in a shoe comprising a sole, a force actuating mechanism, the receiver and a controller, the sole having a top surface for supporting the foot of the user when being worn by the user, the force actuating mechanism being operable to provide a force normal to the top surface of the sole, the force actuating mechanism being disposed at the sole so as to provide the force to a plantar venous plexus of the foot;

generating, via the controller, a control signal to control the force actuating mechanism; and modifying, via the controller, the control signal based on the received blood pressure signal.

18. The non-transitory, tangible, computer-readable media of claim 17, the computer-readable instructions being capable of being read by a computer and being capable of instructing the computer to perform the method, wherein the force actuating mechanism comprises a surface portion and an extending mechanism, wherein the extending mechanism is operable to extend the surface portion from a first position to a second position, wherein the second position is separated from the first position by a distance and in a direction normal to the top surface of the sole, and wherein said modifying the control signal comprises modifying the control signal so as to change the distance between the first position and the second position based on the received blood pressure signal.

19. The non-transitory, tangible, computer-readable media of claim 17, the computer-readable instructions being capable of being read by a computer and being capable of instructing the computer to perform the method, wherein the force actuating mechanism comprises a surface portion and an extending mechanism, wherein the extending mechanism is operable to extend the surface portion from a first position to a second position, wherein the second position is separated from the first position by a distance and in a direction normal to the top surface of the sole, and wherein said modifying the control signal comprises modifying the control signal so as to change the time for the extending mechanism to extend the surface portion from the first position to the second position based on the received blood pressure signal.

20. The non-transitory, tangible, computer-readable media of claim 17, the computer-readable instructions being capable of being read by a computer and being capable of instructing the computer to perform the method further comprising:

receiving, via the receiver, a second blood pressure signal after the controller modifies the control signal based on the received blood pressure signal; and modifying, via the controller, the previously modified control signal based on the received second blood pressure signal.

* * * * *